United States Patent [19]

Pasarela

[11] 4,313,940
[45] Feb. 2, 1982

[54] GRANULAR PESTICIDAL COMPOSITIONS OF DECREASED DERMAL TOXICITY AND METHODS FOR PREPARING THE SAME

[75] Inventor: Nunzio R. Pasarela, Bridgewater, N.J.

[73] Assignee: American Cyanamid Company, Stamford, Conn.

[21] Appl. No.: 151,022

[22] Filed: May 19, 1980

[51] Int. Cl.³ .............................................. A01N 57/00
[52] U.S. Cl. .................................... 424/215; 424/225
[58] Field of Search ................................ 424/215, 225

[56] References Cited

U.S. PATENT DOCUMENTS 3,468,984  9/1969  Beriger ............................. 424/225
3,961,043  6/1976  Huvar ............................... 424/225
4,000,271  12/1976  Kremer et al. .................... 424/225
4,059,700  11/1977  Lindsay ............................ 424/216

FOREIGN PATENT DOCUMENTS 848945  8/1970  Canada ............................... 424/225
46-27000  5/1971  Japan ................................ 424/225

*Primary Examiner*—Douglas W. Robinson
*Attorney, Agent, or Firm*—H. G. Jackson

[57] ABSTRACT

There are provided granular pesticidal compositions which comprise O,O-diethyl-S-(t-butylthio)methyl phosphorodithioate, a vegetable oil such as soybean oil, and a corncob grit carrier. Such compositions are distinguished by decreased mammalian dermal toxicity.

7 Claims, No Drawings

GRANULAR PESTICIDAL COMPOSITIONS OF DECREASED DERMAL TOXICITY AND METHODS FOR PREPARING THE SAME

The present invention relates to granular pesticidal compositions. More particular, it relates to compositions comprising in combination: O,O-diethyl-S-(t-butylthio)methyl phosphorodithioate, a vegetable oil, and a corncob grit carrier. Still more particularly, the invention relates to the aforementioned compositions which are distinguished by decreased mammalian dermal toxicity.

It is known that O,O-diethyl-S-(t-butylthio)methyl phosphorodithioate is a valuable broad spectrum pesticide, often formulated as a 2.5% to 5%, by weight, of granular formulation. Such granular formulation has the advantage that they may be admixed with the seeds of crops, such as rape seeds, and be broadcast simultaneously with said seeds at the rate of from about 0.2 kg to about 2.0 kg per hectare active component so as to control lepidopterous and coleopterous insects which spend a part of their life cycle in the soil. Unfortunately, the pesticidal compound is highly toxic and may be rapidly absorbed by contact through the skin, and thus represents a distinct hazard. It would be highly desirable, therefore, if formulations of said pesticide could be made less toxic to homothermic animals (by dermal contact) while retaining its full potency against insect pests of crops it is designed to control. Such formulations would fulfill a long sought need in the art.

It has been found, unexpectedly, that by incorporating into a granular formulation of a pesticide, tall oil, a vegetable oil such as soybean oil, corn oil and the like, or a fatty acid, such as a tall oil fatty acid and mixtures thereof, in amounts ranging from about one-half to about two times, by weight, of said pesticide present in the formulation, a composition is obtained with markedly reduced mammalian dermal toxicity.

In general, from about 2% by weight to about 10%, by weight, and preferably from 2.5% to 5%, by weight, of the formulation of O,O-diethyl-S-(t-butylthio)methyl phosphorodithioate is mixed with from about 1%, by weight, to about 20%, by weight, and, preferably, 1% to 10%, by weight, of tall oil or a vegetable oil selected from soybean oil and corn oil, or a fatty acid, such as tall oil fatty acid, and mixtures thereof, and the thus obtained toxicant and aforementioned oil or fatty acid mixture is sprayed on rapidly agitated corncob grits of approximately 10/14 to 10/30 mesh size, representing the balance of the formulation (to 100%).

When the spraying is completed, the mixture is agitated until all the liquid is absorbed. If desired, a small amount (0.5% to 1% by weight) of fumed silica powder, talc or an inert solid lubricant can be added to the finished formulation to increase its flowability.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Corncob grits (9965.3 g; 10/14 mesh size) are tumbled and sprayed with a mixture of O,O-diethyl-S-(t-butylthio)methyl phosphorodithioate (692.35 g of 86.5% pure=598.88 g or 5.25% by weight of composition) and soybean oil (692.35 g or 6.1% by weight of composition). After the spraying is completed, the composition is agitated for a short period of time until all of the liquid is absorbed. The thus prepared compositions show an approximately 40% to 75% reduction in acute dermal toxicity in male albino rabbits.

EXAMPLE 2

Corncob grits (10/14 mesh) are tumbled and sprayed with a predetermined amount of the toxicant: O,O-diethyl-S-(t-butylthio)methyl phosphorodithioate or mixtures thereof with various amounts of soybean oil. After the spraying is completed, tumbling is continued for a short period of time to assure uniform distribution.

| Component | Composition of samples g | % w/w | |
|---|---|---|---|
| Sample 1 | | | |
| Toxicant (86.5% pure) | 692.35 | 6.1 | (5.25) |
| Corncob grits, 10/14 mesh | 10,657.65 | 93.9 | |
| | 11,350.0g | 100.0% | |
| Sample 2 | | | |
| Toxicant (86.5% pure) | 692.35 | 6.1 | (5.25) |
| Soybean oil | 346.175 | 3.05 | |
| Corncob grits, 10/14 mesh | 10,322.825 | 90.95 | |
| | 11,350.0g | 100.0% | |
| Sample 3 | | | |
| Toxicant (86.5% pure) | 692.35 | 6.1 | (5.25) |
| Soybean oil | 692.35 | 6.1 | |
| Corncob grits, 10/14 mesh | 9,965.30 | 87.80 | |
| | 11,350.0g | 100.0% | |

EXAMPLE 3

Preparation of granular formulations having decreased dermal toxicity

Corncob grits (10/30 mesh), are agitated and tumbled and are being sprayed with a mixture of a predetermined amount of the toxicant: O,O-diethyl-S-(t-butylthio)methyl phosphorodithioate and soybean oil. After spraying is completed, the formulations are tumbled an additional 10 minutes to assure uniform distribution.

| Component | Composition of samples g | % w/w | |
|---|---|---|---|
| Sample 1 | | | |
| Toxicant (88-71% pure) | 31.0 | 3.1 | (2.75% real) |
| Soybean oil | 55.0 | 5.5 | |
| Corncob grits, 10/30 mesh | 914.0 | 91.4 | |
| | 1,000.0g | 100.0% | |
| Sample 2 | | | |
| Toxicant (88.71% pure) | 61.0 | 6.1 | (5.41% real) |
| Soybean oil | 110.0 | 11.0 | |
| Corncob grits, 10/30 mesh | 829.0 | 82.9 | |
| | 1,000.0g | 100.0% | |

Sample 2 was somewhat wet after preparation, and thus 0.5%, by weight, of silica powder added to improve flowability.

EXAMPLE 4

Corncob grits (14/20 mesh) are being tumbled and while being in motion are sprayed with a mixture of a predetermined amount of the toxicant: O,O-diethyl-S(t-butylthio)methyl phosphorodithioate and soybean oil. After the spraying is completed, the samples are agitated for an additional short period of time to assure uniform distribution.

| Composition of samples | | |
|---|---|---|
| Component | g | % w/w |
| Sample 1 (2.5% real) | | |
| Toxicant (87.1% pure) | 12.4 | 3.1 (2.7) |
| Soybean oil | 12.4 | 3.1 |
| Corncob grits, 14/20 | 375.2 | 93.8 |
| | 400.0g | 100.0% |
| Sample 2 (5.0% real) | | |
| Toxicant (87.1% pure) | 24.4 | 6.1 (5.3) |
| Soybean oil | 24.4 | 6.1 |
| Corncob grits, 14/20 | 351.2 | 87.8 |
| | 400.0g | 100.0% |

EXAMPLE 5

Preparation of various formulation utilizing a corncob grit carrier and the toxicant of the invention Corncob grits (10/30 mesh) are agitated and tumbled and while being in motion, a mixture of a predetermined amount of the toxicant: O,O-diethyl-S-(t-butylthio)-methyl phosphorodithioate and the selected diluent is sprayed onto same.

The composition of the samples is, as follows:

| Component | #1 | #2 | #3 | #4 |
|---|---|---|---|---|
| Toxicant (86.5% pure) | 6.1% | 6.1% | 6.1% | 6.1% |
| White mineral oil | 6.1% | — | — | — |
| Tall oil fatty acid | — | 6.1% | — | — |
| Tall oil | — | — | 6.1% | — |
| Crude Soybean oil | — | — | — | 6.1% |
| Corncob grits, 10/30 | 87.5% | 87.5% | 87.5% | 87.5% |
| | 100.0% | 100.0% | 100.0% | 100.0% |

EXAMPLE 6

General Method for the Evaluation of dermal toxicity of the granular formulations of Examples 1 to 4, using male albino rabbits as test animals Materials 1. Five male albino rabbits weighing approximately 2.2 to 3.5 kilograms are selected for each dosage level. The hair is shaved from the entire trunk.

2. Saran Tubing or "Vinylite" film, VU 1900, 300 millimeters wide, 0.04 millimeters in thickness and long enough to fit around the rabbit.

3. One felt cloth bandage measuring approximately 230×460 millimeters.

4. Four pieces of adhesive tape, each 40 millimeters wide and approximately 360 millimeters long.

Procedure

1. The test material is moistened with water and placed on the plastic film.

2. The animals belly is moistened with water, and it is then placed on the plastic film so as to bring its belly in close contact with the test material. The film is then wrapped around the animal and secured to the animals body with adhesive tape.

3. The felt cloth is then placed under the belly and brought up around the animal and secured with the two remaining strips of adhesive tape.

Evaluation

Twenty-four hours after dosing, the "cuff" is removed and any remaining material is brushed away. If the test material cannot be removed, the animal is fitted with a fiber collar which prevents the animal from licking the treatment area. The animals are observed for 14 days, post dosing, noting signs of toxicity, skin irritation and mortality. At the end of 14 days, the animals are sacrificed and weighed. The data obtained are averaged in Table I below.

TABLE I

| Dermal toxicity ($LD_{50}$ - mg/kg) data of formulations of the invention | | | |
|---|---|---|---|
| Toxicant: diluent weight ratios | Diluent | $LD_{50}$ mg/kg | Remarks |
| 1:0 | — | 149 | single test |
| 1:1 | mineral oil | 171 | single test |
| 1:1 | tall oil | 208 | average of two tests |
| 1:0.5 | soybean oil | 260 | single test |
| 1:1 | soybean oil | 232 | average of three tests |
| 1:2 | soybean oil | 226 | single test |

We claim:

1. A particulated, pesticidal composition comprising: 2% by weight to 10% by weight of O,O-diethyl-S-(t-butylthio)methyl phosphorodithioate, 1% by weight to 20% by weight of tall oil or a vegetable oil selected from the group consisting of soybean oil and corn oil, or tall oil fatty acids, and sufficient amount of corncob grits to total said composition to 100%.

2. The composition according to claim 1, wherein the amount of said pesticide is 2.25% to 5.5%, and the amount of vegetable oil is 3% to 6.5%.

3. The composition according to claim 1, wherein the amount of said pesticide is 5.25%, the amount of vegetable oil is 3.05%, and said vegetable oil is soybean oil.

4. The composition according to claim 1, wherein the amount of said pesticide is 5.25%, the amount of vegetable oil is 6.1%, and said vegetable oil is soybean oil.

5. The composition according to claim 1, wherein the amount of said pesticide is 2.75%, the amount of vegetable oil is 5.5% and said vegetable oil is soybean oil.

6. The composition according to claim 1, wherein tall oil is employed.

7. The composition according to claim 1, wherein tall oil fatty acid is employed.

* * * * *